United States Patent
Clark

(10) Patent No.: US 9,541,484 B2
(45) Date of Patent: Jan. 10, 2017

(54) FASTENER STRETCH MEASUREMENT FIXTURE

(71) Applicant: Toyota Motor Engineering & Manufacturing North America, Inc., Erlanger, KY (US)

(72) Inventor: Christopher T. Clark, San Antonio, TX (US)

(73) Assignee: Toyota Motor Engineering & Manufacturing North America, Inc., Erlanger, KY (US)

(*) Notice: Subject to any disclaimer, the term of this patent is extended or adjusted under 35 U.S.C. 154(b) by 216 days.

(21) Appl. No.: 14/272,336

(22) Filed: May 7, 2014

(65) Prior Publication Data

US 2015/0323402 A1 Nov. 12, 2015

(51) Int. Cl.
| | |
|---|---|
| G01N 3/08 | (2006.01) |
| G01B 21/16 | (2006.01) |
| G01B 5/00 | (2006.01) |
| G01L 5/00 | (2006.01) |

(52) U.S. Cl.
CPC .............. *G01N 3/08* (2013.01); *G01B 5/0004* (2013.01); *G01B 21/16* (2013.01); *G01L 5/00* (2013.01)

(58) Field of Classification Search
CPC .............. G01B 21/16; G01L 5/00; G01N 3/08
See application file for complete search history.

(56) References Cited

U.S. PATENT DOCUMENTS

| | | | | |
|---|---|---|---|---|
| 2,651,196 A | * | 9/1953 | Pinkel | G01B 5/30 261/69.1 |
| 3,354,705 A | * | 11/1967 | Dyer, Jr. | G01L 5/0042 73/761 |
| 4,333,351 A | * | 6/1982 | Bickford | G01L 5/24 411/14 |
| 4,413,518 A | | 11/1983 | Jones | |
| 4,530,143 A | | 7/1985 | Casarcia | |
| 4,719,804 A | * | 1/1988 | Maruyama | G01N 3/00 73/761 |
| 5,499,540 A | | 3/1996 | Whaley et al. | |
| 5,792,961 A | * | 8/1998 | Giebner | G01N 3/08 73/786 |
| 5,913,647 A | * | 6/1999 | Hodge | F16B 31/028 116/DIG. 34 |
| 5,948,994 A | * | 9/1999 | Jen | G01N 3/08 73/796 |
| 7,001,123 B2 | | 2/2006 | Kersten | |

(Continued)

*Primary Examiner* — Lisa Caputo
*Assistant Examiner* — Punam Roy
(74) *Attorney, Agent, or Firm* — Christopher G. Darrow; Darrow Mustafa PC

(57) ABSTRACT

Fixtures and methods are described herein to measure fastener stretch after fastener application. The measurement fixtures may include fastener contacting portions having contact plates that may move orbitally about a measurement shaft to allow contact plates to abut against non-parallel end surfaces of a fastener. The fixtures may also include datum assemblies that have datum plate mounted in fixed relation to the contacting portions that allow for measurements to be made between the datum plates. Adjustable dials may be included to transfer rotational movement of the dial to translation movement of the contacting portions. Measurement fixtures may further include a frame and mounting portions.

19 Claims, 3 Drawing Sheets

(56) References Cited

U.S. PATENT DOCUMENTS

| | | | |
|---|---|---|---|
| 7,260,998 B2* | 8/2007 | Madden | G01L 5/24 73/761 |
| 8,534,132 B1* | 9/2013 | Purdy | F16B 31/02 73/761 |
| 2002/0059840 A1* | 5/2002 | Houston | G01L 1/2206 73/862.474 |
| 2015/0377755 A1* | 12/2015 | Semsi | G01N 3/08 73/826 |
| 2016/0003721 A1* | 1/2016 | Seok | G01N 3/02 73/821 |

* cited by examiner

FASTENER STRETCH MEASUREMENT FIXTURE

BACKGROUND OF THE DISCLOSURE

The present disclosure relates generally to measurement fixtures and, more particularly, to fixtures capable of measuring fastener length changes.

Varieties of fasteners are utilized in several industries to mechanically affix two or more objects together. For example, automobiles require the use of many different fasteners to join together different vehicle components. As a result, it may be important to analyze fastener characteristics both before and after tightening or attaching to ensure the quality of joints. Fastener length may be measured to analyze the stretch of fasteners after tightening or attaching the fastener to assess torque set point and bolt relaxation. Such information may provide insight to axial tension in order to assess assigned torque values and give confidence that a torque setting on process equipment is creating a desired axial tension in the fastener. Additionally, length measurements may provide bolt relaxation data to determine how fastened joint characteristics change over time.

Many procedures for detecting and measuring fastener stretch involve the use of elaborate and expensive ultrasonic equipment, and can be time and resource intensive. Additionally, such procedures may require the processing or changing of fastener surface characteristics rendering them unfit for use on a completed vehicle or other finished product.

SUMMARY OF THE DISCLOSURE

Embodiments of fixtures and methods for measuring fastener fastened length changes are described herein. Measurement fixtures may include contact portions configured to abut against end surfaces of a fastener that have contact plates allowed to move orbitally about a longitudinal axis. The fixtures may also include adjustable portions for moving the contact portions relative to each other as well as datum surfaces in fixed relation to the contact plates. The fixtures may also include a frame for retaining components and mounting the fixture.

In one implementation, a fastener stretch measurement fixture may comprise a first contact portion and a second contact portion, each configured to abut against an end of a fastener, an adjusting portion configured to adjust the position of the first contact portion relative to the second contact portion, and a first datum plate and a second datum plate, wherein the first datum plate is attached in fixed relation to the first contact portion and the second datum plate is attached in fixed relation to the second contact portion, each datum plate defining a substantially planar datum face.

In another implementation, a fastener stretch measurement fixture may comprise a first contact portion and a second contact portion, each configured to abut against an end of a fastener. Each contact portion may comprise a contact plate having a contact surface, a swivel joint, and a mounting shaft, the swivel joint being attached to the mounting shaft and the contact plate allowing for orbital movement of the contact plate about a longitudinal axis of the mounting shaft. The fixture may further comprise a first adjusting portion and a second adjusting portion, each adjusting portion comprising a rotatable dial configured to adjust the position of the contact portions relative to each other upon rotational movement of the dial. The fixture may further comprise a first datum plate and a second datum plate, wherein the first datum plate is attached in fixed relation to the first contact portion and the second datum plate is attached in fixed relation to the second contact portion, each datum plate defining a substantially planar datum face.

In yet another implementation, a method for measuring fastener stretch may comprise the steps of positioning a measuring fixture around a fastener such that a first contact portion of the measuring fixture faces a first end of the fastener and a second contact portion of the measuring fixture faces a second end of the fastener, abutting a first contact face of the first contact portion against the first end of the fastener and a second contact face of the second contact portion against the second end of the fastener, and measuring a first distance between a first datum plate and a second datum plate, wherein the first datum plate is attached in fixed relation to the first contact portion and the second datum plate is attached in fixed relation to the second contact portion.

The foregoing features and elements may be combined in various combinations without exclusivity unless expressly indicated otherwise. These features and elements as well as the operation thereof will become more apparent in light of the following description and the accompanying drawings. It should be appreciated, however, that the following description and drawings are intended to be exemplary in natures and non-limiting.

BRIEF DESCRIPTION OF THE DRAWINGS

The description makes reference to the accompanying drawings wherein like reference numerals refer to like parts throughout the several views, and wherein.

DETAILED DESCRIPTION

Fixtures are described herein that allow for the measurement of fastener lengths both before and after fastener application. The measurement fixtures may include fastener contacting portions having contact plates that may move orbitally about a measurement shaft to allow contact plates to abut against non-parallel end surfaces of a fastener. The fixtures may also include datum assemblies that have a datum plate mounted in fixed relation to the contacting portions that allow for measurements to be made between the datum plates. Adjustable dials may be included to transfer rotational movement of the dial to translation movement of the contacting portions. Measurement fixtures may further include a frame and mounting portions.

Embodiments disclosed having contact plates with orbital movement may eliminate abutting plane error present in non-parallel surfaces at fastener ends and do not require any processing or preparation of the fastener. Fixtures may normalize the variation of parallelism between the ends by separating datum surfaces from contact surfaces.

As used herein, the term "fastener" may include any hardware device that is capable of mechanically joining two or more physical objects together having two exterior measurement surfaces. Fasteners may be described with reference to the figures as bolts, but further non-limiting examples of fasteners may include pins, screws, clips, and rivets.

Figure 1:
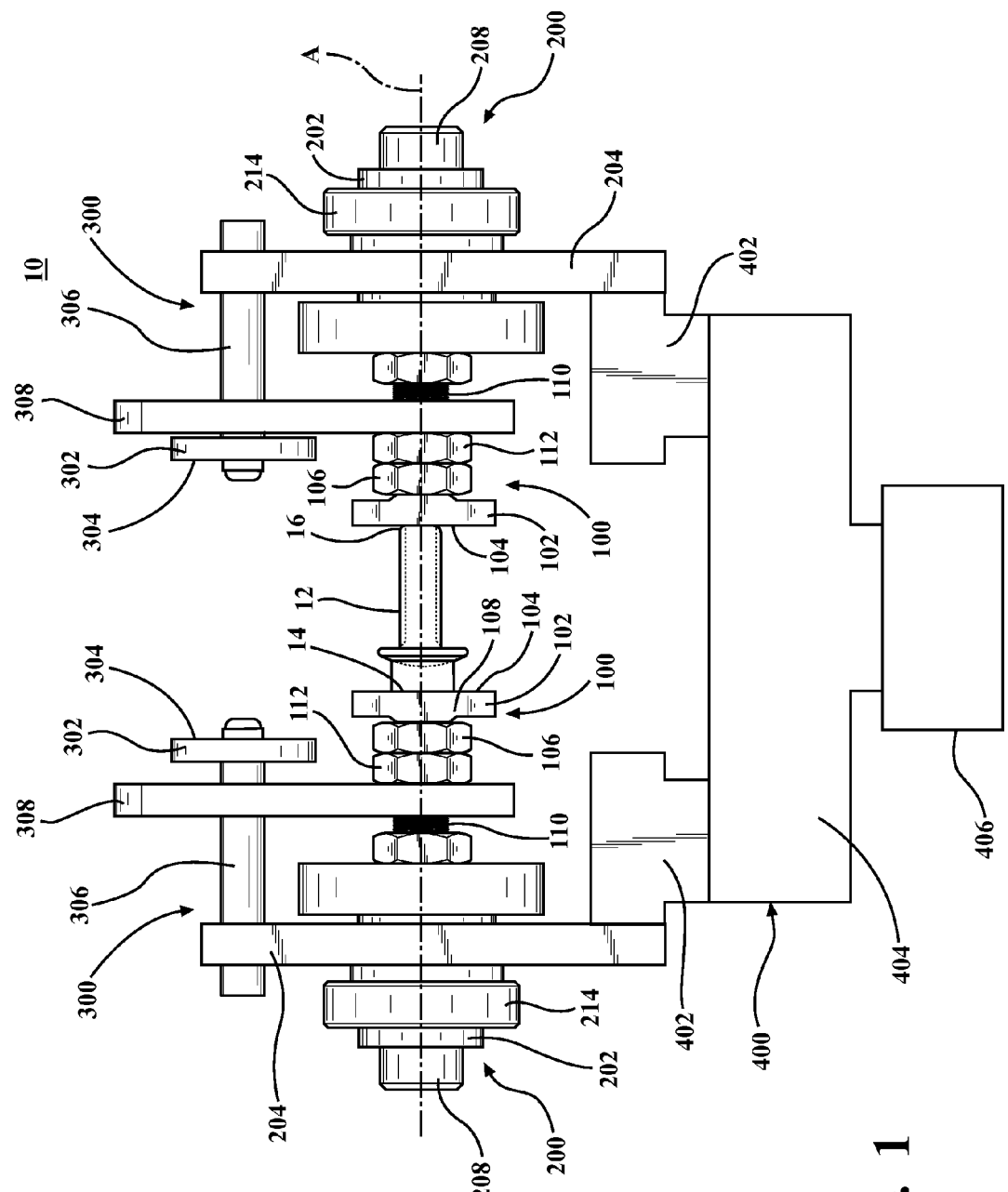
FIG. 1 shows a perspective view of a fastener measuring fixture.

FIG. 1 shows a perspective view of measuring fixture 10, with exemplary fastener 12. Measuring fixture 10 may generally include one or more of a contact portion 100, adjustable portion 200, datum assembly 300, and frame 400.

In some embodiments, measuring fixture 10 may include one or more contact portions 100 that are configured to contact a surface of fastener 12. For example, measuring fixture 10 may include two contact portions 100 that may contact a first end 14 and a second end 16 of fastener 12. Fastener 12 may generally align with an axis A when in a measuring position.

In some embodiments, contact assembly 100 may include a contact plate 102 with a contact face 104. Contact face 104 may be substantially planar and configured to contact and abut against either first end 14 or second end 16 of fastener 12. Contact face 104 may abut against fastener 12 when in abutment with a plane defined by a surface or multiple points of first or second end 14/16. For example, contact face 104 may abut against fastener 12 through the abutment of contact face 104 with three or more points on first end 14.

Figure 2:
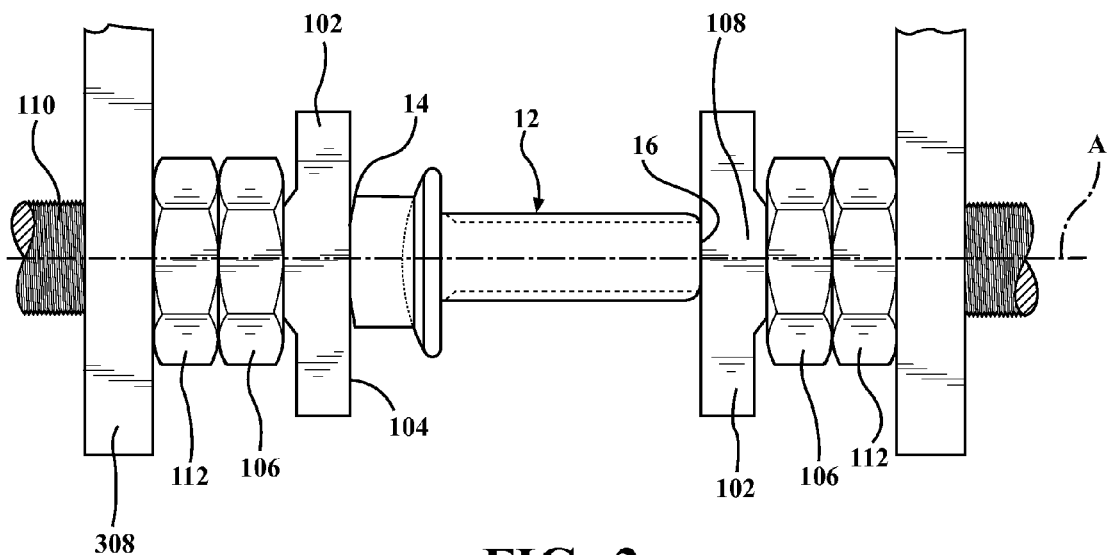
FIG. 2 shows a partial perspective view of fastener contact assemblies of the fastener measuring fixture of FIG. 1.
Figure 3:
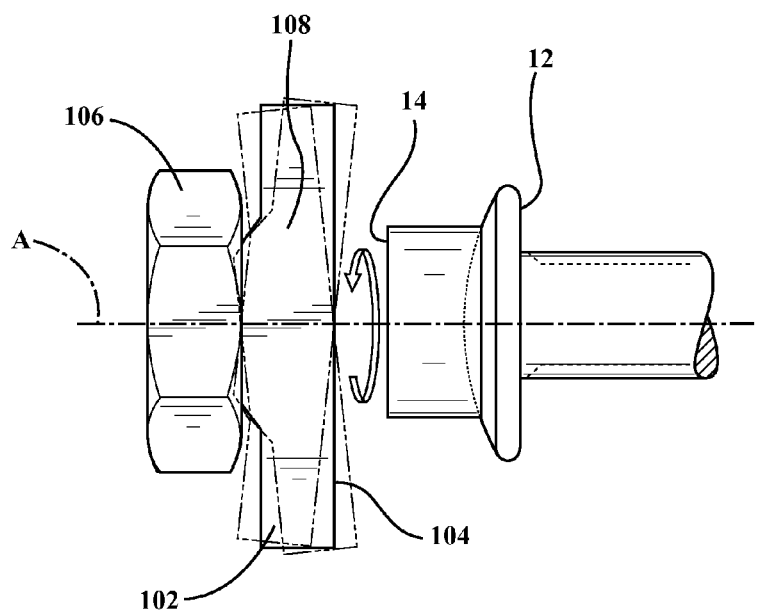
FIG. 3 shows a partial perspective view of one of the fastener contact assemblies showing orbital movement of a fastener contact plate.
Figure 4:
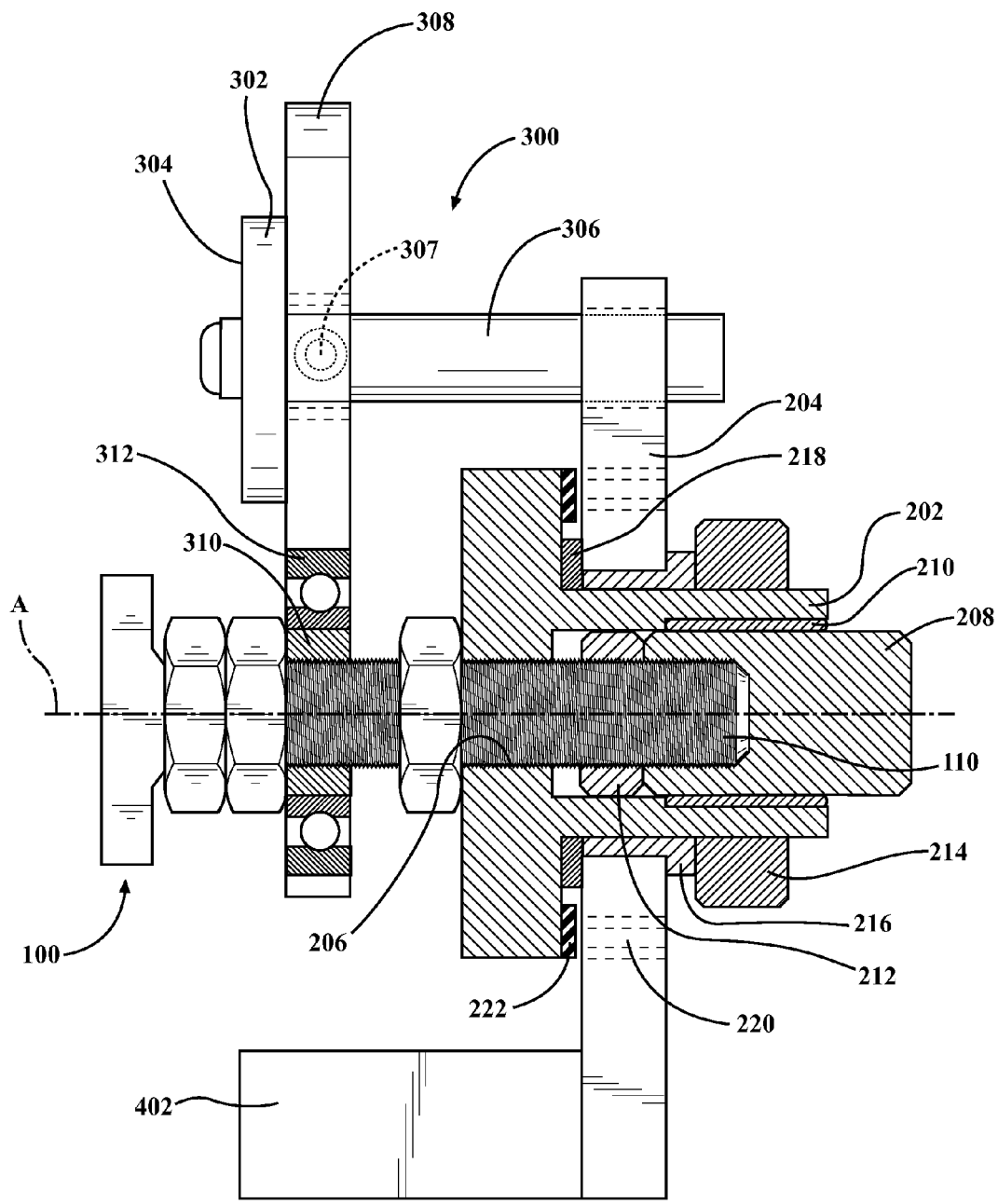
FIG. 4 shows a partial cross sectional view of an adjustment assembly of the fastener measuring fixture of FIG. 1.

With reference to FIGS. 2 and 3, contact portions 100 may be further described. In some embodiments, contact plate 102 may be attached to a swivel joint 106. Swivel joint 106 may include a moveable end 108 that may be attached to contact plate 102. For example, moveable end 108 may be pressed into contact plate 102. As a result, contact plate 102 may have moveable freedom in orbital directions about axis A.

In some embodiments, contact portion 100 may include a mounting shaft 110, and contact plate 102 may be located near an end of mounting shaft 110. Mounting shaft 110 may have a radial outer surface that is threaded to engage components of contact portion 100. For example, swivel joint 106 may include an inner radial surface at an end opposing moveable end 108 having threads capable of engaging with mounting shaft 110. Contact portion 100 may include a lock nut 112 capable of being threaded onto mounting shaft 110 and retaining swivel joint 106 in a particular fixed position along mounting shaft 110.

Referring now to FIG. 3, contact plate 102 may be allowed to swivel about axis A and orbitally move such that contact plate 102 may move through different angles relative to axis A. This may allow contact plate 102 to move slightly to engage and abut against an end of fastener 12. For example, if first or second end 14/16 is not smooth and perpendicular to axis A, contact plate 102 may move slightly to contact three or more points on first or second end 14/16 to abut against fastener 12. Thus, the need to process or prepare surfaces of fastener 12 before contact portion 100 abuts against fastener 12 may be alleviated.

In some embodiments, measuring fixture 10 may include at least one adjustable portion 200 to allow for movement of contact portion 100 and datum assembly 300. For example, adjustable portion 200 may allow for contact portion 100 to move in a direction along axis A, either towards or away from fastener 12. As shown in FIG. 1, measuring fixture 10 may include a pair of symmetrical adjustable portions 200. It is also contemplated that fixture 10 may have only one adjustable portion 200 on one side while the other contact portion 100 may be fixed in relation to frame 400.

In some embodiments, adjustable portion 200 includes dial 202 that is contained in dial mount 204. Dial mount 204 may be fixedly attached to frame 400. For example, dial 202 may be surrounded and captured by a bearing 216 that allows for dial 202 to be rotatable about axis A without moving translationally. Dial 202 may include dial threads 206 sized to engage the threads on mounting shaft 110. In some embodiments, adjustable portion 200 may include a collar 214 that may be clamped to dial 202 to prevent dial 202 from wobbling in relation to axis A. Bushing 218 may be included in adjustable portion 200 to assist in locating and retaining dial 202 in a fixed position with respect to dial mount 204.

Adjustable portion 200 may include an adjuster shaft 208 that is connected to mounting shaft 110 in fixed relation thereto via adjuster locknut 212. Adjuster shaft 208 may be partially captured within a dial aperture and may contact a sleeve 210. The outside radial surface of adjuster shaft 208 and inside radial surface of sleeve 210 may be substantially smooth. Thus, adjuster shaft 208 and sleeve 210 may act as a plain or journal bearing to allow for precise and controlled movement of measurement shaft 110 in relation to dial 202. Lubrication may be included between surfaces of adjuster shaft 208 and sleeve 210.

During operation, dial 202 may be rotated by a user about axis A. The engagement and interaction between dial threads 206 and mounting shaft 110 may cause mounting shaft 110 to spin about axis A and move along the direction of axis A relative to dial 202. This may cause contact plate 102 of contact portion 100 to be displaced in the same direction.

In some embodiments, dial mount 204 may include apertures 220 sized for dial retaining members. For example, dial retaining members may include screws configured to engage threads in apertures 220. Dial 202 may include gasket 222 located such that a retaining member may pass through aperture 220 towards gasket 222. The retaining member may contact and slightly deform gasket 222. Such contact between the retaining member and gasket 222 may prevent or resist the rotational movement of dial 202 such that measurement shaft 110 and contact portion 100 may be "locked" into a particular position relative to dial 202 without interrupting orientation to axis A previously established.

While the embodiments of the figures are described with dials 202 that may be configured to rotatably adjust mounting shaft 110, it is contemplated other designs may be utilized. For example, adjustable portion 200 may include sliding portions that may be configured to move transversely along axis A to adjust the position of contact portion 100.

In some embodiments, fixture 10 may include datum assemblies 300 to allow for measurement information to be detected. For example, datum assemblies 300 may include a datum plate 302 having a datum face 304 shown on one side but might be on either or both sides of 302. Datum plate 302 may be fixedly attached to a datum shaft 306. Datum shaft 306 may extend in a longitudinal direction parallel to axis A as seen in FIG. 1. Datum shaft 306 may extend through datum support 308. For example, datum support 308 may be attached to measurement shaft 110 via support bearing 312 near one end and may receive datum shaft 306 via an aperture near a distal end. A set screw may be incorporated into datum support 308 to fix datum shaft 306 within support 308. For example, a set screw may be contained in support aperture 307. Datum shaft 306 may be supported by and extend through dial mount 204.

Datum support 308 may be attached to mounting shaft 110 such that datum support mount 310 is attached to mounting shaft 110 and is moved translationally as mounting shaft 110 is moved along axis A. Datum support bearing 312 allows for mounting shaft 110 to move rotationally with respect to datum support 308, and allows datum support 308 to remain in a particular angular direction with respect to axis A while moved translationally along axis A. That is, datum support 308 may be moved transversely along axis A as mounting shaft 110 is adjusted and remains in fixed relation to contact portion 100.

Datum plates 302 may be positioned such that datum faces 304 generally oppose each other and are substantially parallel and perpendicular to axis A. Datum face 304 may be a smooth surface. The distance between datum plates 302 may be measured using mechanical or electrical measuring instruments. For example, calipers may be used to measure the distance between datum faces 304 of datum plates 302 subsequent to the abutment of contact plates 102 with fastener 12.

Frame 400 may indirectly connect contact portions 100 together in fixture 10. Frame 400 may include mounting attachment 402 connected to dial mount 204. Frame 400 may further include frame connection 404 to connect a pair of mounting attachments 402 together as shown. Furthermore, frame 400 may include fixture attachment 406 to allow for fixture 10 to be attached to other structure depending on application. For example, fixture 10 may be attachable to a variety of fixtures within an automotive plant through fixture attachment 406. It is contemplated that frame 400 may include substantially rigid materials such as high strength polymers or metals. Portions of the frame 400 may be detachable and/or adjustable to be configured for a variety of fixture 10 applications.

A process or method for measuring fastener lengths may be described with reference to measuring fixture 10. However, steps in accordance with this disclosure can occur in various orders and/or concurrently. Additionally, steps in accordance with this disclosure may occur with other steps not presented and described herein. Furthermore, not all illustrated steps may be required to implement a method in accordance with the disclosed subject matter.

Fixture 10 and fastener 12 may be positioned such that fastener 12 is positioned substantially along the same longitudinal axis as contact portions 100 and measuring shafts 110. Contact portions 100 may be abutted against each end of fastener 12 by moving contact plates 102 toward the fastener 12 using adjustable portions 200 until contact plates 102 abut ends of fastener 12. For example, dials 202 may be turned to move contact plates 102 toward the ends of fastener 12.

Subsequent to the abutment of contact plates 102 with the ends of fastener 12, a distance may be measured and recorded between datum plates 302. For example, calipers may be used to determine the distance between datum faces 304.

One or both of contact portions 100 may be moved away from fastener 12 by adjustable portions 200. Fastener 12 may be tightened or otherwise applied to finish the particular joint application. For example, fastener 12 may be a bolt that may be tightened upon the application of a particular torque.

Subsequent to tightening, fixture 10 may be used to measure and record the distance between datum plates 302. For example, the positioning, abutting, and measuring steps may be repeated. A difference in distance may be determined that reflects a fastener change in length measurement.

The foregoing description relates to what are presently considered to be the most practical embodiments. It is to be understood, however, that the disclosure is not to be limited to these embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A fastener stretch measurement fixture, comprising:
   a first contact portion and a second contact portion, each configured to abut against an end of a fastener;
   an adjusting portion configured to adjust the position of the first contact portion relative to the second contact portion; and
   a first datum plate and a second datum plate, wherein the first datum plate is attached in fixed relation to the first contact portion and the second datum plate is attached in fixed relation to the second contact portion, each datum plate having a datum face,
   wherein each contact portion includes:
      a mounting shaft;
      a swivel joint having a first end and a second end, the first end attached to the mounting shaft; and
      a contact plate having a contact face, wherein the contact plate is attached to the second end of the swivel joint such that the contact plate may be moved orbitally relative to a longitudinal axis of the mounting shaft.

2. The fixture of claim 1, wherein the adjusting portion comprises a rotatable dial.

3. The fixture of claim 2, wherein the adjusting portion further comprises an adjusting shaft attached to the mounting shaft and a sleeve, wherein the adjusting shaft is in contact with the sleeve within an aperture in the rotatable dial.

4. The fixture of claim 1, further comprising a second adjusting portion configured to adjust the position of the second contact portion.

5. The fixture of claim 4, further comprising a frame connecting both adjusting portions.

6. The fixture of claim 1, wherein the mounting shaft is threadingly attached to the swivel joint and the adjusting portion.

7. The fixture of claim 6, wherein the adjusting portion comprises a rotatable dial threadingly engaged with the mounting shaft such that rotation of the dial causes the mounting shaft to move translationally in relation to the dial along the longitudinal axis.

8. The fixture of claim 1, wherein the datum faces of the first and second datum plates generally oppose each other and are substantially parallel.

9. The fixture of claim 1, wherein each of the first and second datum plates are attached to a datum shaft having a longitudinal axis parallel to the longitudinal axis of the mounting shaft.

10. A fastener stretch measurement fixture, comprising:
    a first contact portion and a second contact portion, each configured to abut against an end of a fastener, wherein each contact portion comprises a contact plate, a swivel joint, and a mounting shaft, a first portion of the swivel joint being attached to the mounting shaft and a second portion of the swivel joint being attached to the contact plate allowing for orbital movement of the contact plate about a longitudinal axis of the mounting shaft;
    a first adjusting portion and a second adjusting portion, each adjusting portion comprising a rotatable dial configured to adjust the position of the contact portions relative to each other upon rotational movement of the dial; and a first datum plate and a second datum plate, wherein the first datum plate is attached in fixed relation to the first contact portion and the second datum plate is attached in fixed relation to the second contact portion, each datum plate defining a substantially planar datum face.

11. The fixture of claim 10, wherein the dial is threadingly engaged with the mounting shaft such that rotation of the dial causes the mounting shaft to move translationally in relation to the dial along the longitudinal axis of the mounting shaft.

12. The fixture of claim 10, wherein the contact plate comprises at least one contact face that is substantially planar.

13. The fixture of claim 10, wherein each of the mounting shafts of the first and second contact portions share the same longitudinal axis.

14. The fixture of claim 10, wherein the datum faces of the first and second datum plates oppose each other and are substantially parallel.

15. The fixture of claim 10, wherein each of the first and second datum plates are attached to a datum shaft having a longitudinal axis parallel to the longitudinal axis of the mounting shaft.

16. A method for measuring fastener stretch, comprising the steps of:
   positioning a measuring fixture around a fastener such that a first contact portion of the measuring fixture faces a first end of the fastener and a second contact portion of the measuring fixture faces a second end of the fastener;
   abutting a first contact face of the first contact portion against the first end of the fastener and a second contact face of the second contact portion against the second end of the fastener;
   measuring a first distance between a first datum plate and a second datum plate, wherein the first datum plate is attached in fixed relation to the first contact portion and the second datum plate is attached in fixed relation to the second contact portion;
   removing the fixture from the fastener;
   tightening the fastener;
   repositioning the measuring fixture around the fastener such that the first contact portion of the measuring fixture faces the first end of the fastener and the second contact portion of the measuring fixture faces the second end of the fastener;
   abutting the first contact face of the first contact portion against the first end of the fastener and the second contact face of the second contact portion against the second end of the fastener;
   measuring a second distance between the first datum plate and the second datum plate; and
   determining a difference between the first distance and second distance.

17. The method of claim 16, wherein each contact portion comprises a contact plate attached to a mounting shaft.

18. The method of claim 16, wherein abutting comprises adjusting the position of at least one of the contact portions by rotating a dial threadingly engaged to a mounting shaft.

19. A fastener stretch measurement fixture, comprising:
   a first contact portion having a first mounting shaft and a first contact plate orbitally connected to the first mounting shaft via a first swivel joint;
   a second contact portion having a second mounting shaft and a second contact plate orbitally connected to the second mounting shaft via a second swivel joint;
   an adjusting portion configured to adjust the position of the first contact plate relative to the second contact plate; and
   a first datum plate and a second datum plate, wherein the first datum plate is attached in fixed relation to the first contact plate and the second datum plate is attached in fixed relation to the second contact plate.

* * * * *